United States Patent [19]

Peet et al.

[11] 4,052,385

[45] Oct. 4, 1977

[54] CERTAIN N-(2-HYDROXYETHYL)-HETEROIMINOCARBOXAMIDES

[75] Inventors: Norton P. Peet; Shyam Sunder, both of Midland, Mich.

[73] Assignee: The Dow Chemical Company, Midland, Mich.

[21] Appl. No.: 624,365

[22] Filed: Oct. 21, 1975

[51] Int. Cl.$^2$ .................. C07D 207/16; C07D 211/16; C07D 223/04; C07D 295/20

[52] U.S. Cl. ............................ 260/239 BF; 544/169; 544/137; 260/268 C; 260/268 H; 260/293.67; 260/293.76; 260/293.86; 260/307 F; 260/326.4; 424/244; 424/248.54; 424/250; 424/267; 424/272

[58] Field of Search ......... 260/326.4, 239 BF, 293.76, 260/293.86

[56] References Cited

U.S. PATENT DOCUMENTS

| | | | |
|---|---|---|---|
| 2,857,430 | 10/1958 | Applegath et al. | 260/326.4 |
| 3,804,853 | 4/1974 | D'Amico et al. | 260/326.4 |

OTHER PUBLICATIONS

Trepanier et al, J. Med. Chem., vol. 13, pp. 729–733 (1970).

*Primary Examiner*—Alton D. Rollins
*Attorney, Agent, or Firm*—James W. Ambrosius

[57] ABSTRACT

Novel N-(2-hydroxyethyl)heteroiminocarboxamides are described. The compounds are pharmacodynamically active and serve as intermediates for the preparation of corresponding 2-amino-2-oxazolines which are active pharmacodynamically.

6 Claims, No Drawings

CERTAIN N-(2-HYDROXYETHYL)HETEROIMINOCARBOXAMIDES

SUMMARY OF THE INVENTION

The present invention is directed to N-(2-hydroxyethyl)heteroiminocarboxamides having the general formula:

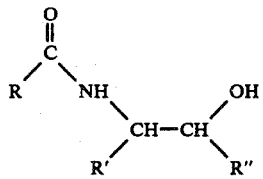

wherein R represents
- 1-pyrrolidino
- 1-piperidino
- 1-(2-methyl)piperidino
- 1-(3-methyl)piperidino
- 1-(4-methyl)piperidino
- 4-morpholino
- 1-hexamethyleneimino
- 1-(4-methyl)piperazino
- 1-(2,6-dimethyl)piperidino
- 1-heptamethyleneimino
- 1-(4-phenyl)piperazino:

R' represents hydrogen, an alkyl group of from 1 to about 4 carbon atoms, or phenyl;

and R" represents hydrogen, an alkyl group of from 1 to about 4 carbon atoms, or phenyl.

From time to time hereinafter, these compounds are referred to by the general term, hydroxyethylurea.

The compounds of the present invention are normally clear liquids or white solids. They are soluble both in organic solvents and in water. Member compounds of the invention are used as intermediates for the preparation of 2-amino-2-oxazolines which have been shown to be highly active pharmacodynamically. Certain of the present compounds have been found to display some anticonvulsive, antidepressant, and antiplatelet aggregation activity of their own. Additionally certain members have been found to demonstrate herbicidal and antifungal activity and are useful in various agricultural applications such as the control and killing of noxious weeds and plant parasites. It is recognized, however, that not all of the compounds of the invention exhibit the same degree of activity nor are all of the species active in all the areas.

Prior Art

The technology for the general preparation of hydroxyethylureas and their use as intermediates for the preparation of oxazolines is not new in the art. Frump, J. A. Chem. Reviews, 71, 483 (1971); Chem.Abstracts, 71:101842 x; and D. L. Trepanier, et al, J. Med. Chem., 13, 729 (1970). The hydroxyethylureas of the present invention owe their novelty to the cycloamino moieties.

DETAILED DESCRIPTION OF THE INVENTION

The hydroxyethylureas of the present invention are prepared by reacting a selected carbamoyl chloride with an amino alcohol according to the following reaction.

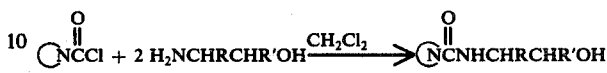

As indicated hereinbefore, the resulting hydroxyethylurea products of the present invention may be utilized as intermediates in that they can be cyclized by treatment with thionyl chloride in an inert solvent to produce the corresponding substituted 2-amino-2-oxazolines as shown in the reaction below.

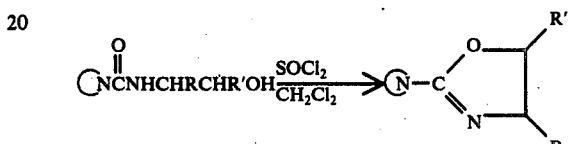

These substituted oxazolines have been found to be particularly active as CNS-depressants, CNS-stimulants, platelet aggregation inhibitors, anticonvulsive agents, and blood cell anti-sickling agents.

EXAMPLE 1

General Preparation of hydroxyethylureas of the Present Invention

A 0.1 mol. quantity of a selected amino alcohol and a 0.1 mol. quantity of a trialkylamine, preferably triethylamine, are dissolved in ca. 200 ml. of an inert solvent, preferably methylene chloride ($CH_2Cl_2$). The resulting solution is cooled in an icebath. A 0.1 mol. quantity of the appropriate carbamoyl chloride in ca. 20 ml. of the inert solvent is added, and the reaction mixture is stirred at 25° C. for 10 hrs. The mixture is washed with water and/or saturated potassium carbonate ($K_2CO_3$) solution, dried with sodium sulfate ($Na_2SO_4$), and concentrated to leave either a clear liquid or a white solid. The solid hydroxyethylurea product is normally recrystallized as a white solid from ethanol (EtOH), $CH_2Cl_2$, ethanol-ethyloxide (EtOH—$Et_2O$), or methylene chloride-ethyloxide ($CH_2Cl_2$—$Et_2O$).

Following the procedure as set forth directly hereinbefore, a number of hydroxyethylureas were prepared having the general formula:

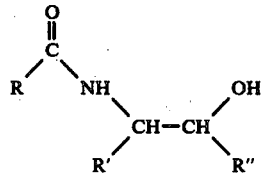

Table I summarizes the results from these studies.

TABLE I

| Example No. | R | R' | R" | MP °C | % Yield | Recrystn. Solvent | Empirical Formula | Mol. Wt. |
|---|---|---|---|---|---|---|---|---|
| 2 | 1-pyrrolidino | H | $CH_3$ | 87–89 | 46 | EtOH—$Et_2O$ | $C_8H_{16}N_2O_2$ | 172.22 |
| 3 | 1-piperidino | H | $CH_3$ | 72–73 | 60 | EtOH—$E_2O$ | $C_9H_{18}N_2O_2$ | 186.25 |
| 4 | 1-(2-Me)piperidino | H | $CH_3$ | liquid | 93* | | $C_{10}H_{20}N_2O_2$ | 200.28 |
| 5 | 1-(3-Me)piperidino | H | $CH_3$ | liquid | 92* | | $C_{10}H_{20}N_2O_2$ | 200.28 |

TABLE I-continued

| Example No. | R | R' | R'' | MP ° C | % Yield | Recrystn. Solvent | Empirical Formula | Mol. Wt. |
|---|---|---|---|---|---|---|---|---|
| 6 | 1-(4-Me)piperidino | H | $CH_3$ | liquid | 99* |  | $C_{10}H_{20}N_2O_2$ | 200.28 |
| 7 | 4-morpholino | H | $CH_3$ | 103–104 | 95* | EtOH | $C_8H_{16}N_2O_3$ | 188.22 |
| 8 | 1-hexamethyleneimino | H | $CH_3$ | 59–61 | 45 | EtOH—$E_2O$ | $C_{10}H_{20}N_2O_2$ | 200.28 |
| 9 | 1-pyrrolidino | $C_2H_5$ | H | liquid | 99* |  | $C_9H_{18}N_2O_2$ | 186.25 |
| 10 | 1-piperidino | $C_2H_5$ | H | liquid | 99* |  | $C_{10}H_{20}N_2O_2$ | 200.28 |
| 11 | 1-(2-Me)piperidino | $C_2H_5$ | H | liquid | 93* |  | $C_{11}H_{22}N_2O_2$ | 214.30 |
| 12 | 1-(3-Me)piperidino | $C_2H_5$ | H | liquid | 97* |  | $C_{11}H_{22}N_2O_2$ | 214.30 |
| 13 | 1-(4-Me)piperidino | $C_2H_5$ | H | liquid | 99* |  | $C_{11}H_{22}N_2O_2$ | 214.30 |
| 14 | 4-morpholino | $C_2H_5$ | H | 112.5–113.5 | 99* | EtOH | $C_9H_{18}N_2O_3$ | 202.25 |
| 15 | 1-hexamethyleneimino | $C_2H_5$ | liquid | 93* |  |  | $C_{11}H_{22}N_2O_2$ | 214.30 |
| 16 | 1-pyrrolidino | H | $C_6H_5$ | 136–138 | 88 | EtOH—$Et_2O$ | $C_{13}H_{18}N_2O_2$ | 234.29 |
| 17 | 1-piperidino | H | $C_6H_5$ | 95–97 | 92 | $CH_2Cl_2$—$Et_2O$ | $C_{14}H_{20}N_2O_2$ | 248.30 |
| 18 | 1-(2-Me)piperidino | H | $C_6H_5$ | 66–72 | 96* |  | $C_{15}H_{22}N_2O_2$ | 262.34 |
| 19 | 1-(3-Me)piperidino | H | $C_6H_5$ | 87–90 | 74 | EtOH—$Et_2O$ | $C_{15}H_{22}N_2O_2$ | 262.34 |
| 20 | 1-(4-Me)piperidino | H | $C_6H_5$ | 133–134 | 83 | EtOH—$Et_2O$ | $C_{15}H_{22}N_2O_2$ | 262.34 |
| 21 | 4-morpholino | H | $C_6H_5$ | 115–117 | 64 | $CH_2Cl_2,Et_2O$ | $C_{13}H_{18}N_2O_3$ | 250.29 |
| 22 | 1-hexamethyleneimino | H | $C_6H_5$ | 105–106 | 95 | EtOH—$Et_2O$ | $C_{15}H_{22}N_2O_2$ | 262.34 |
| 23 | 1-pyrrolidino | $CH_3$ | $C_6H_5$ | 142–144 | 60 | EtOH | $C_{14}H_{20}N_2O_2$ | 248.32 |
| 24 | 1-piperidino | $CH_3$ | $C_6H_5$ | 146–148 | 74 | $CH_2Cl_2$ | $C_{15}H_{22}N_2O_2$ | 262.30 |
| 25 | 1-(2-Me)piperidino | $CH_3$ | $C_6H_5$ | 114–116 | 73 | EtOH—$Et_2O$ | $C_{16}H_{24}N_2O_2$ | 276.37 |
| 26 | 1-(3-Me)piperidino | $CH_3$ | $C_6H_5$ | 88–89 | 79 | $CH_2Cl_2$—$Et_2O$ | $C_{16}H_{24}N_2O_2$ | 276.37 |
| 27 | 1-(4-Me)piperidino | $CH_3$ | $C_6H_5$ | 110–112 | 76 | EtOH—$Et_2O$ | $C_{16}H_{24}N_2O_2$ | 276.37 |
| 28 | 4-morpholino | $CH_3$ | $C_6H_5$ | 157–159 | 75 | $CH_2Cl_2$ | $C_{14}H_{20}N_2O_3$ | 264.30 |
| 29 | 1-hexamethyleneimino | $CH_3$ | $C_6H_5$ | 144–145 |  | $CH_2Cl_2$—$Et_2O$ | $C_{16}H_{24}N_2O_2$ | 276.37 |

*Crude yield

EXAMPLE 30

Preparation of N-(1-methyl-2-phenyl-2-hydroxyethyl)-4-morpholinecarboxamide (See Example 28, Table I).

A solution of 15.2 grams of norephedrine in 200 ml. of $CH_2Cl_2$ was cooled to 0–5° C. To this 11.0 grams of triethylamine was added with stirring. To the stirred mixture a solution of 14.9 grams of morpholine carbonyl chloride in 10 ml. of $CH_2Cl_2$ was added dropwise. The mixture was then stirred for 2 hours and left to stand at room temperature for 16 hours. The mixture was washed with water and the organic layer was dried over anhydrous sodium sulfate. The organic layer was then filtered and evaporated to a small volume. The hydroxyethylurea, N-(1-methyl-2-phenyl-2-hydroxyethyl)-4-morpholinecarboxamide was filtered off as a white solid and recrystallized from $CH_2Cl_2$.

EXAMPLE 31

Preparation of 4-(4,5-dihydro-4-methyl-5-phenyl-2-oxazolyl)morpholine from N-(1-methyl-2-phenyl-2-hydroxyethyl)-4-morpholinecarboxamide.

A solution of 10.6 grams of the hydroxyethylurea prepared in Example 30 in 200 ml. of $CH_2Cl_2$ was cooled to 0° C. Thionyl chloride (5.36 grams) dissolved in 20 ml. of $CH_2Cl_2$ was added, and the mixture was heated at reflux temperature for 30 minutes. The mixture was left at room temperature for 64 hours. The solvent was evaporated under vacuum to leave a yellow gum. This material was dissolved in water. Concentrated $K_2CO_3$ solution was added to make the solution basic. The 4-(4,5-dihydro-4-methyl-5-phenyl-2-oxazolyl)morpholine separated out as an oil. The oil was dissolved in $CH_2Cl_2$, washed with water, and dried over anhydrous $Na_2SO_4$. The solution was filtered and evaporated to an oil.

EXAMPLE 32

Control of Apple Scab using N-(2-hydroxypropyl)-2-methyl-1-piperidinecarboxamide Example 4, Table I).

Host plants were divided into two groups, innoculated with Apple Scab (*Venturia inaequalis*), and placed under conditions conducive to infection, i.e. low temperature and high humidity. Two days after innoculation the test plants were treated with an aqueous solution containing 100 ppm of the above referenced hydroxyethylurea. Control plants remained untreated. The plants were returned to high humidity conditions for the remainder of the infection period. When symptoms were well developed, the plants were graded for disease control. The untreated checks are rated as "no control" and the absence of disease at "100% control". The hydroxyethylurea gave 90% disease control under these conditions.

The following hydroxyethylurea compounds of the present invention were also found to be effective fungicides for the control of Apple Scab.

Hexahydro-N-(2-hydroxypropyl)-1H-azepine-1-carboxamide (Example 8, Table I).
N-(2-hydroxy-2-phenylethyl)-2-methyl-1-piperidinecarboxamide (Example 18, Table I).
N-(2-hydroxy-2-phenylethyl)-4-methyl-1-piperidinecarboxamide (Example 20, Table I). N-(2-hydroxy-1-methyl-2-phenylethyl)-4-methyl-piperidinecarboxamide (Example 27, Table I).

EXAMPLE 33

Use of N-(2-hydroxy-1-methyl-2-phenylethyl)-1-pyrrolidinecarboxamide (Example 23, Table I) as a platelet aggregation inhibitor.

Emboli formed in the capillary beds of mice caused by the administration of ADP (adenosine 5'-diphosphate) result in a stroke-like response that prevents mice from staying on an inclined screen. Ten mice were dosed orally (30 mg/kg) with N-(2-hydroxy-1-methyl-2-phenylethyl)-1-pyrrolidinecarboxamide. Five control mice were injected via the tail vein with 0.05 mole/kg. of ADP to test the effectiveness of the challenge. One hour after compound administration the test mice are challenged with ADP (as above) and placed on an inclined screen. Unprotected mice are unable to maintain their position on the screen due to a stroke-like response caused by platelet aggregation. At the end of the test five more untreated mice are challenged with ADP to test the effectiveness of the challenge. N-(2-hydroxy-1-methyl-2-phenylethyl)-1-pyrrolidinecarboxamide was found to be 60% effective in protecting challenged mice.

N-(2-hydroxypropyl)-1-pyrrolidinecarboxamide (Example 2, Table I) may be used as a platelet aggregation inhibitor in the same manner as described above.

We claim:

1. The compound N-(2-hydroxypropyl)-1-pyrrolidinecarboxamide.

2. The compound N-(2-hydroxypropyl)-2-methyl-1-piperidinecarboxamide.

3. The compound Hexahydro-N-(2-hydroxypropyl)-1H-azepine-1-carboxamide.

4. The compound N-(2-hydroxy-2-phenylethyl)-4-methyl-1-piperidinecarboxamide.

5. The compound N-(2-hydroxy-1-methyl-2-phenylethyl)-4-methyl-piperidinecarboxamide.

6. The compound N-(2-hydroxy-1-methyl-2-phenylethyl)-1-pyrrolidine carboxamide.

* * * * *

UNITED STATES PATENT AND TRADEMARK OFFICE
CERTIFICATE OF CORRECTION

PATENT NO. : 4,052,385
DATED : October 4, 1977
INVENTOR(S) : Norton P. Peet, et al.

It is certified that error appears in the above-identified patent and that said Letters Patent are hereby corrected as shown below:

First page, line under ABSTRACT "Novel" should read --Certain--.

Column 2, line 32, "hydroxyethylureas" should read --Hydroxyethylureas--.

Column 2, lines 64 - 69, Table 1, Example No. 3, under the subheading Recrystn. Solvent, should read --EtOH-Et$_2$O--.

Column 4, Table 1, Example No. 8, under the subheading Recrystn. Solvent should read --EtOH-Et$_2$O--.

Column 3, Table 1, Example No. 15, under the subheading R" "liquid" should read --H--.

Column 3, Table 1, Example No. 15, under the subheading MP° C "93*" should read --liquid--.

Column 4, Table 1, Example No. 15, under the subheading % Yield should read --93*--.

Column 4, Table 1, Example No. 15, under the subheading Empirical Formula "214.30" should read --$C_{11}H_{22}N_2O_2$--.

Column 4, Table 1, Example No. 15, under the subheading Mol. Wt. should read --214.30--.

Column 4, Table 1, Example No. 29, under the subheading % Yield "$CH_2Cl_2$-$Et_2$O" should read --84--.

UNITED STATES PATENT AND TRADEMARK OFFICE
CERTIFICATE OF CORRECTION

PATENT NO. : 4,052,385

DATED : October 4, 1977

INVENTOR(S) : Norton P. Peet, et al.

It is certified that error appears in the above-identified patent and that said Letters Patent are hereby corrected as shown below:

Column 4, Table 1, Example No. 29, under the subheading Recrystn. Solvent "$C_{16}H_{24}N_2O_2$" should read --$CH_2Cl_2$-$Et_2O$--.

Column 4, Table 1, Example No. 29, under the subheading Empirical Formula "276.37" should read --$C_{16}H_{24}N_2O_2$--.

Column 4, Table 1, Example No. 29, under the subheading Mol. Wt. should read --276.37--.

Column 4, line 45, after Table I). start a new paragraph.

Signed and Sealed this

*Seventh* Day of *February 1978*

[SEAL]

*Attest:*

RUTH C. MASON
*Attesting Officer*

LUTRELLE F. PARKER
*Acting Commissioner of Patents and Trademarks*